United States Patent [19]

Cerami et al.

[11] Patent Number: 4,788,149

[45] Date of Patent: Nov. 29, 1988

[54] PROTEOLYTIC ENZYME FROM BLOOD-SUCKING NEMATODES AND ITS USES AS AN ANTICOAGULANT AS A VACCINE AND AS AN ANTITHELMINIC AGENT

[75] Inventors: Anthony Cerami, Flanders, N.J.; Peter Hotez, New York, N.Y.

[73] Assignee: The Rockefeller University, New York, N.Y.

[21] Appl. No.: 696,856

[22] Filed: Jan. 30, 1985

Related U.S. Application Data

[63] Continuation-in-part of Ser. No. 490,103, Apr. 29, 1983, abandoned.

[51] Int. Cl.$^4$ .......................... C12N 9/48; C12N 9/66; C12N 9/50; C12N 9/64
[52] U.S. Cl. .................................... 435/212; 435/218; 435/219; 435/226
[58] Field of Search ................. 435/212, 240, 241, 68, 435/69, 70, 948

[56] References Cited

PUBLICATIONS

Oya et al., *Biol. Abst.*, Abstract No. 40125, 1978, "Some Properties of Hemoglobin Protease from *Ancylostoma caninum*".
McLaren et al., *Int. J. Parasit.*, 1974, vol. 4, pp. 39–46, "The Anterior Glands of Adult *Necator americanus* (Nematoda: Strongyloidea)—II Cytochemical and Functional Studies".
Matthews, *Z Parasitenkd*, 1982, vol. 68, pp. 81–86, "Skin Penetration by *Necator americanus* Larvae".
Hotez et al., *J. Exp. Med.*, vol. 157, May 1983, pp. 1594–1603, "Secretion of an Anticoagulant by Ancylostoma Hookworms".
Hotez et al., *J. Biol. Chem.*, vol. 260(12), Jun. 25, 1985, pp. 7343–7348, "Isolation and Characterization of a Proteolytic Enzyme from the Adult Hookworm *Ancylostoma caninum*".
Hotez et al., *J. Cell Biochem.*, Supp. 10, (10 P&A), 1986, p. 132, "Isolation, Cloning, and Expression of a Protease from Ancylostoma Hookworms".

*Primary Examiner*—Thomas G. Wiseman
*Assistant Examiner*—Robin Lyn Teskin
*Attorney, Agent, or Firm*—Klauber & Jackson

[57] ABSTRACT

This invention relates to proteolytic enzymes with elastolytic properties from blood-sucking nematodes (hereinafter called HP enzymes). These enzymes are useful an anti-coagulants and as a means for dissolving fibrin clots. Because of their importance in the mechanism by which blood-sucking nematodes obtain nutrients from the host, HP enzymes would be an effective vaccine for prevention and treatment of these parasites. For the same reason, substances which inhibit HP enzymes would also be effective antithelminic agents.

5 Claims, 2 Drawing Sheets

PROTEOLYTIC ENZYME FROM BLOOD-SUCKING NEMATODES AND ITS USES AS AN ANTICOAGULANT AS A VACCINE AND AS AN ANTITHELMINIC AGENT This application is a continuation-in-part of application Ser. No. 490,103, filed Apr. 29, 1983, now abandoned.

This invention relates to proteolytic enzymes with elastolytic properties from blood-sucking nematodes (hereinafter called HP enzymes). These enzymes are useful as anti-coagulants and as a means for dissolving fibrin clots. Because of their importance in the mechanism by which blood-sucking nematodes obtain nutrients from the host, HP enzymes would be an effective vaccine for prevention and treatment of these parasites. For the same reason, substances which inhibit HP enzymes would also be effective antithelminic agents.

BACKGROUND

Human hookworm disease, a clinical condition caused by *Ancylostoma duodenale* or *Necator americanus* infection, affects an estimated 950 million people in the developing world (Banwell, J. G., and G. A. Schad. 1978. *Clinics in Gastroenterology* 7:129). The adult parasites, using their buccal cavities and hooklike teeth, attach themselves to villi in the small intestine. Each worm can then extract up to 0.20 ml of blood per day causing intestinal blood loss and ultimately iron-deficiency anemia and hypoalbuminemia in the host. (Roche, M., and M. Layrisse. 1966. *Am. J. Trop. Med. Hyg.* 15:1031; Miller, T. A. 1968. *Roy. Soc. Trop. Med. Hyg.* 62:473).

Although it is possible to cure hookworm infection by known anthelminic agents, widespread infestation of the human and canine population persists. Of the approximately 50 million dogs currently living in the United States a large percentage have hookworm infection. An effective vaccine would eliminate this persistent parasite in canine carriers and in human carriers as well.

Gamma-irradiated larvae of *Ancylostoma caninum* have been used as a vaccine against canine hookworm. Although the vaccine was produced and marketed, it did not prove to be commercially successful due in part to a short shelf-life (Miller T., (1971) *Ad. Parasitology* 9:153). Accordingly, a safe, effective and commercially feasible vaccine for prevention and treatment of hookworm infection has been sought.

An interesting and provocative aspect of infection by blood sucking nematodes is the fact that the parasites are able to prevent blood coagulation while feeding (Loeb, L. and M. S. Fleisher. 1910. *J. Infec. Dis.* 7:625). To date the biochemical mechanism which allows hookworms to prevent blood coagulation while feeding remains unexplained. Previous studies have shown that extracts of the dog hookworm *Ancylostoma caninum* can prolong prothrombin time, with variable effects on partial thromboplastin time, and interfere with collagen or ADP-induced platelet aggregation, as well as inhibit the action of factor Xa (Spellman, G.G., and H. L. Nossel. 1971. *Am. J. Physiol.* 220:922).

A proteolytic enzyme with anticlotting properties has recently been found in the giant leech *Haementeria ghilianii* (Budzynski, A. Z., Olexa, S. A., Brizuela, B. S., Sawyer, R. T., and G. S. Stent. 1981. *Proc. Soc. Exp. Biol. Med.* 168:266). A similar proteolytic anticoagulant has been sought in the Ancylostoma hookworms and other blood-sucking nematodes.

SUMMARY

This invention reports the discovery of a proteolytic anticoagulant in secretory products and homogenates of blood-sucking nematodes. Proteolytic enzymes (HP enzymes) having elastolytic properties may be isolated from blood-sucking nematodes. An HP enzyme has been isolated fron Ancylostoma hookworms which has elastolytic properties and a molecular weight of about 37,000 daltons. Smaller fragments of the enzyme may also have proteolytic properties. The HP enzyme may be prepared by gel electrophoresis or column chromatography of either homogenates or secretory products of blood-sucking nematodes such as Ancylostoma hookworms.

HP enzyme may also be produced by preparing biological chimerae of the HP-producing gene from a blood-sucking nematode, e.g. Ancylostoma hookworm, and a suitable vector by genetic engineering. HP enzyme may be isolated from growing cultures of these genetically engineered clones. Polypeptides or parts thereof having the amino acid sequence of the HP gene may be prepared by chemical synthesis. In addition, nucleic acid hybrids having all or part of the genetic sequence of the HP enzyme-producing gene, can be synthesized and introduced into an appropriate vector. This hybrid becomes a template for synthesis of polypeptides having the amino acid sequence of HP enzymes in toto or in part.

HP enzyme, because of its unique proteolytic properties is useful for inhibiting the clotting of plasma. It also may be used therapeutically to dissolve fibrin clots. Fragments of the HP enzyme and synthesized polypeptides having the amino acid sequence of the HP enzyme or parts thereof may be used likewise as an anti-clotting agent or clot dissolving agent.

With suitable adjuvants HP would be a vaccine against blood-sucking nematode infection in mammals, particularly dogs and humans. Immunization with HP enzyme vaccine would both prevent and treat these parasitic infections. HP enzyme fragments and synthesized polypeptides having the amino acid sequence of HP enzyme may also be used as vaccine. It should also be possible to treat diseases caused by blood-sucking nematodes by administering to a mammal infested with these parasites substances which inhibit HP enzymes. Examples of such anthelminic agents are antibodies to the HP enzymes—both naturally occuring antibodies isolated from serum and the more specific monoclonal antibodies. Chemically synthesized compounds which are inhibitory substrates for the enzyme will also be suitable anthelminic agents.

DETAILS

Figure 1:
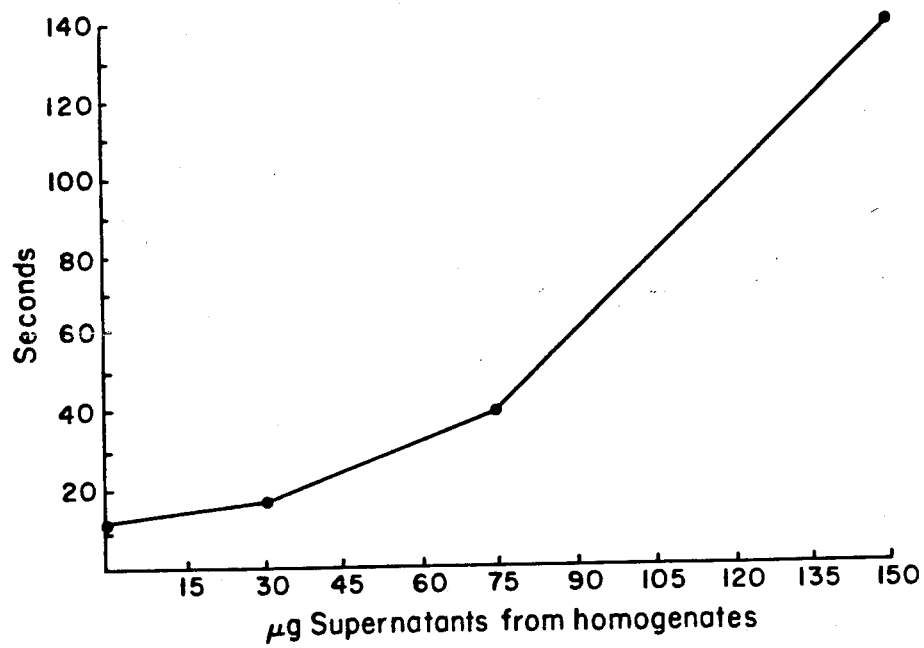
FIG. 1 illustrates the influence of *A. duodenale* homogenates on the prothrombin time of normal human plasma.

The present invention concerns proteolytic, elastolytic enzymes (HP enzymes) in blood-sucking nematodes. In particular, an HP enzyme of about 37,000 dalton molecular weight from Ancylostoma hookworm is described. HP enzymes may be isolated from homogenates of worms prepared by mechanically mincing the worms, as in a tissue grinder, and centrifuging the minced material to sediment and remove solids. This homogenate when subjected to electrophoresis, on SDS polyacrylamide gel slabs, for instance, separates into 5 major bands which may be identified by proteolytic activity. *A. caninum* homogenates separates into approximately 40 major bands by this method. *A. duodenale* shows similar patterns of electrophoretic activity.

HP enzymes may also be isolated from the excretory/secretory (ES) products of the worms. In this method, the worms are incubated in buffered saline solution containing antibodies or RPMI - 1640 defined medium until viability ceases, about 24 hours. The solution is centrifuged to remove debris and is then subjected to electrophoresis. The bands which may be identified by proteolytic activity correspond to those from the worm homogenates. It is possible also to isolate HP enzymes from worm homogenates and ES by means of column chromatography. In this method, eluted fractions are monitored for proteolytic activity to indicate the presence of the HP enzymes.

A preferred embodiment of the present invention comprises the 37,000 dalton molecular weight HP enzyme from *A. caninum*. This HP enzyme may be isolated by electrophoresis or column chromatography of worm homogenates or ES products. This HP enzyme exhibits proteolytic and elastolytic properties characteristic of HP enzymes which makes it an effective anticoagulant and agent for fibrinolysis. The fibrinolytic activity of this HP enzyme makes it especially useful as a therapeutic agent for dissolving blood clots, and inhibiting both histolysis and elastolycity.

HP enzymes may also be prepared by cloning suitable organisms containing the HP-enzyme gene. In this method the gene from a blood-sucking nematode, *A. canimum*, for example, is inserted into a suitable vector to form an HP enzyme producing clone. Suitable vectors include, but are not limited to, bacteria such as *E. coli, B. subtilis,* yeasts and viruses such as SV40 and lambda bacteriophage. HP enzyme is recovered from the extracellular supernatant of the growing cultures by methods known in the art, electrophoresis or column chromatography, for example.

In a similar manner, a nucleic acid hybrid having the sequence of the HP producing gene may be chemically synthesized and inserted into a suitable vector to make an organism which produces HP enzyme. A hybrid coding for fragments of the enzyme may likewise be inserted in a vector to make organisms which produce fragments of the HP enzyme.

The nucleic acid hybrid having sequence of the HP enzyme producing gene is useful as a template in the chemical synthesis of polypeptides having the amino acid sequence of HP enzymes or fragments thereof. One method which may be employed for synthesizing peptides based on nucleic acid sequence of the hybrid is given in Sutcliffe, J. G. et al, *Nature* 287, 801 (1980).

Figure 2:
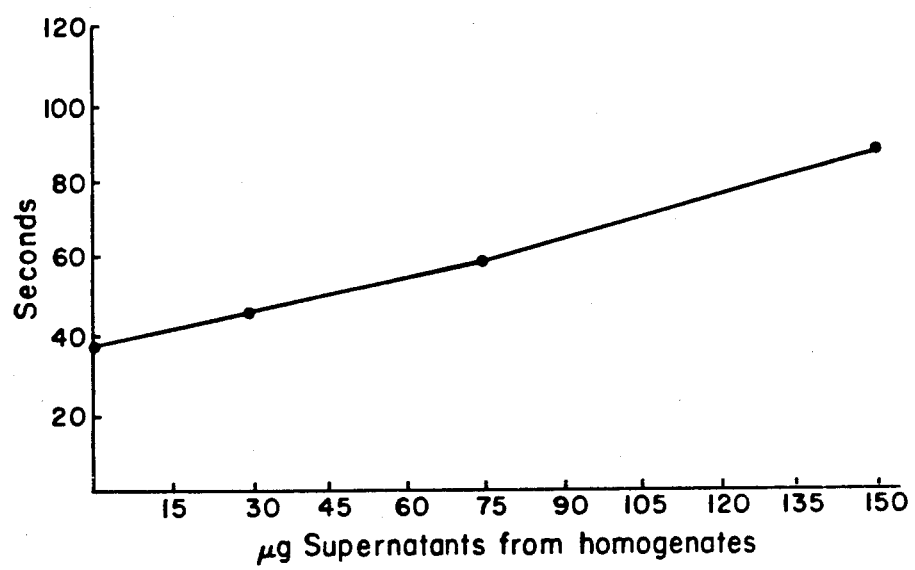
FIG. 2 illustrates the influence of *A. duodenale* homogenates on the partial thromboplastin time of normal human plasma.

The HP enzymes possess proteolytic and fibrinolytic properties that make them useful as anti-coagulants and therapeutic clot dissolving agents. As is illustrated in FIG. 1, the doubling of amount of *A. duodenale* homogenate from 60µg to 120 µg increases the prothrombin time of normal human plasma about 3-fold. The partial thromboplastin time of normal human plasma increases in a concentration dependent manner with *A. duodenale* homogenate as illustrated by FIG. 2. The HP enzymes of *A. caninum* degrade fibrinogen in an amount proportional to the amount of homogenate or ES products added to fibrinogen coated on plates. ES products also cleave plasminogen into fragments which have proteolytic activity. These proteolytic fragments differ in molecular weight from the products of urokinase incubation. Elastolytic activity of the HP enzymes is illustrated by their ability to hydrolyze a synthetic substrate which has specificity for elastolytic enzymes.

The present invention also concerns the use of HP enzymes as vaccines against blood-sucking nematodes. The HP enzymes, in combination with suitable adjuvants, would be effective vaccines against blood-sucking nematode infection. Natural antibodies from the sera of infected animals are known to inhibit proteolytic enzyme activity of extracts of blood-sucking nematodes. HP enzymes administered prophylactically to a mammal would induce natural resistance in the form of antibodies which would inhibit the HP enzymes thus destroying their ability to inhibit clot formation at their feeding site and preventing their ability to attach and to feed on the villi.

HP enzymes isolated from worms or produced by genetically engineered organisms would be suitable vaccines. Fragments of the HP enzyme or polypeptides having the amino acid sequence of the HP enzyme in its entirety or in part would also be suitable vaccines.

A vaccine against hookworm, a commonly occurring blood-sucking nematode would significantly reduce the incidence of human infection in tropical areas where this persistent parasite exerts its debilitating effect. Infection can be both prevented and treated in dogs, and other mammals as well, by vaccination with HP enzymes or its synthetic analogues.

The present invention also concerns anthelminic agents comprising inhibitors of the HP enzymes produced by blood-sucking nematodes. Inhibition of the proteolytic enzymes results in clot formation at the feeding site of the worms and the eventual expulsion of the parasites. Suitable inhibitors which may be administered to humans, dogs or other mammals include antibodies which inhibit the enzyme. The antibodies may be harvested from serum by methods well known in the art or may be monoclonal antibodies produced by the hybridoma technique. Inhibitors may also be chemically synthesized substrates of the HP enzymes or other chemical compounds.

The following examples are intended to illustrate the present invention but it is not intended to be limited thereby.

EXAMPLES

Abbreviations used in these examples. AMC, 7-amino-4-methylcoumarin; ES products, excretory/secretory products; FDP, fibrinogen degradation products; meosucc-ala-ala-pro-val-AMC; methoxysuccinyl-L-alanyl-L-alanyl-Lprolyl-L-valine-4-methylcoumarinyl-7-amide; PAGE, polyacrylamide gel electrophoresis; PBS, phosphate buffered saline; PT, prothrombin time; PTT, partial thromboplastin time; SDS, sodium dodecylsulfate; and TES, N-tris (hydroxymethyl) methyl-2-aminoethane sulfonic acid. Temperatures are in degrees centigrade.

I. Preparation and Characterization of Homogenates and Excretory/Secretory Products From Blood-Sucking Nematodes Nematode Isolation 1000–1500 third-stage infective filariform ($L_3$) larvae of *A. duodenale* were administered to 10-week old beagles reared helminth-naive (White Eagle Laboratories, Doyelstown, Pennsylvania) and immunocompromised with a daily oral dose of 5 mg prednisolone. 42 days after infection, the entire length of the small intestine was removed, slit longitudinally, and suspended in 0.85% NaCl at 37°. Within two hours the majority of adult worms released their grasp and were collected at the bottom of the cylinder. The living worms were individually rinsed in saline and were either used immediately or stored at −80°.

$L_3$ larvae of A. caninum were cultured from embryonated eggs in the feces of infected pups (Nawalinski, T. A., and G. A. Schad. 1974. *Am. J. Trop. Med. Hyg.* 23:895). The $L_3$ larvae (1500–2000) were administered to mongrel pups, aged 2 to 12 months. The pups were sacrificed 20 to 30 days after infection when their hematocrits fell below 25 percent indicating heavy infections with A. caninum. Alternatively, adult A. caninum were obtained from naturally infected pups. The adult worms were collected by the same procedure as for A. duodenale.

Preparation of nematode homogenates and separation of supernatant. Approximately 100 human or dog hookworms were suspended in 1.0 ml of 0.1 M Tris-HCl buffer (pH 8.1) ground in a Tenbroeck tissue grinder (A. H. Thomas Co., Philadelphia), and centrifuged at 1000 rpm for 10 minutes at 4° in an IEC centrifuge. The supernatant (homogenate) was removed and stored at −20°. The homogenate had a protein content of 4.0–8.5 mg/ml when measured according to the method of Bradford (Bradford, M. M. 1976. *Anal. Biochem.* 72:248).

Isolation of Excretory/Secretory (ES) products. ES products from adult A. caninum were isolated using a modified procedure of Day, et al (Day, K. P., Howard, R. J., Prowse, S. J., Chapman, C. B., and G. F. Mitchell. 1979. *Parasite Immunol.* 1:217). Approximately 100–1000 adult worms were incubated in phosphate buffered saline (PBS) containing 100–2000 U/ml penicillin and 100–500 µg/ml streptomycin sulfate at 37° for 22 hours. The viability was 100 per cent (as determined by motility) for the first 12 hours, but began to slowly decline thereafter. At 24 hours approximately 40–75 percent were viable. The fluid was removed from the settled worms and spun at 1000 rpm for 10 minutes at 4° in an IEC centrifuge to remove any debris, and stored at −80°. The ES products had a protein content of 0.05–0.20 mg/ml when measured according to the method of Bradford. Alternatively, aliquots were taken at various times to assess the proteolytic activity of the secreted material.

Anticoagulant Properties of Hookworm Homogenates and ES Products

Clotting times. Prothrombin times were measured at 37° with 0.1 ml of citrated plasma incubated with various concentrations of either homogenates or ES products. 0.20 ml of Simplastin Automated (General Diagnostics, Morris Plains, N.J.) was added to the mixture and the time for clot formation to occur was noted.

Partial thromboplastin times were measured at 37° with 0.1 ml of citrated plasma, 0.1 ml of Automated APTT (General Diagnostics, Morris Plains, N.J.) was added to the mixture and the time for clot formation to occur was noted, after the addition of 0.10 ml of 0.025 M $CaCl_2$.

To determine whether Ancylostoma hookworms had an effect on fibrin clot formation, homogenates of A. duodenale were added to samples of normal citrated human plasma and which were then assayed for prothrombin times (PT) and partial thromboplastin times (PTT). The addition of aliquots of the homogenates prolonged PT and PTT in a concentration dependent manner. A prolongation of prothrombin time was also observed with ES products of A. caninum.

Protein Composition of Homogenates and ES Products Electrophoretic separation of proteolytic activities. The protein composition of the homogenates and ES products were analyzed by SDS-PAGE (Laemmli, U.K. 1970. *Nature.* 227:680) after silver staining. Proteolytic activity in the gels was visualized by a modified procedure of Granelli-Piperno and Reich (Granelli-Piperno, A., and E. Reich. 1978 *J. Exp. Med.* 148:223). Aliquots of hookworm homogenates or ES products were added to 20 µl of a buffer containing 10% glycerol, 3% SDS, and 0.0625 M Tris-HCl buffer, pH 6.8, and placed in an 80° bath for 30 seconds. Samples were loaded onto 10% SDS polyacrylamide slab gels not more than 0.75 mm in thickness and subjected to electrophoresis. After electrophoresis the gel was gently rocked in 2.5% aqueous Triton X-100 for 40 minutes at 22°, rinsed thoroughly with distilled water, and then rocked in distilled water for an additional 30 minutes. At this time the gel was removed and overlayed onto an agar plate containing casein [5.2 ml of 0.1 M Tris-HCl buffer, pH 8.1, 3.6 ml of 2.5% agar, and 2.0 ml of 8% Carnation Instant Milk (boiled 10 minutes in PBS)] and incubated at 37°. Depending on enzyme concentration, bands of lysis corresponding to proteolytic activity appeared in 4–12 hours. These bands were visualized better by staining with amido black, and then destaining with a solution of methanol, acetic acid, and water (70:10:20).

Approximately 40 major bands appeared after silver staining. ES products were also analyzed. Compared to the crude homogenates, ES products contained a fewer number of proteins. All 12 of the secreted proteins could be identified in the homogenates of the adult worms. Both A. caninum homogenates and ES products were separated on SDS-PAGE and overlayed onto casein agar. Examination of proteolytic activity in the homogenates revealed seven bands including three major components at 31,000, 36,000, and 40,000 daltons. Smaller amounts of proteolytic activity were associated with molecular weight bands at 21,000, 71,000, 91,000, and 102,000 daltons. Homogenates of A. duodenale showed a similar pattern of proteolytic activity.

Isolation of HP Enzyme. Only a single band of proteolytic activity was found in the electrophoretically separated ES products of A. caninum. This band is shown in attached FIG. 1. The apparent molecular weight of this protease was 37,000 daltons.

PURIFICATION OF THE ENZYME

Purification of the Enzyme Involves Four Steps.

All of the steps were carried out at 0°–4° C.

Step I: Crude Extract—Approximately 3000 adult hookworms were suspended in 15 ml of 0.01 M sodium phosphate, pH 6.0 (buffer A) and ground in a glass homogenizer on ice for 20 minutes. The hookworm homogenate was centrifuged at 30,000 x g in an ss-34 Sorvall rotor for 1 hour and the clear supernatant was collected. The pellet and lipid layer were re-extracted with 15 ml buffer A, centrifuged as before, and the supernatants were pooled (final volume=38 ml).

Step II: CM-Sepharose CL-6B Chromatography—The combined supernatants were applied onto a 7.5×1.5 cm column of CM-Sepharose CL-6B equilibrated previously with buffer A. The column was then washed (15.5 ml/hour) with 30 ml of buffer A, followed by a linear pH gradient (40 ml), increasing from pH 6.0 to 8.0 in 0.01 M sodium phosphate buffer. The pH gradient was followed by a linear salt gradient (160 ml) increasing from 0 to 0.1 M in sodium chloride and 0.01 M to 0.1 M in sodium phosphate (pH 8.0). Fractions of 7.8 ml were collected. The active fractions 17-21 were pooled and concentrated to 3 ml by pervaporation against water. Insoluble material was removed by centrifugation at 9,000>g for 20 minutes.

Step III: Sephadex G-50 Chromatography—The concentrated solution from Step II was applied on a 50×2.5 cm column of Sephadex G-50equilibrated with a 0.05 M Tris-CHl buffer, pH 7.6 containing 0.2 M NaCl, and 0.005 M $CaCl_2$. The flow rate was 9.8 ml/h. Fractions of 3.3 ml were collected. The enzymatic activity in fractions 51–52 was pooled concentrated to 2.3 ml by pervaporation and rechromatographed on Sephadex G-50 under identical conditions. The eyzymatic activity appearing in fractions 51–52 from both columns was pooled (final volumn=9.6 ml).

Step IV: Phenyl-Sepharose CL-4B Chromatography—The solution from Step III was mixed with an equal volume of 4 M NaCl and applied on a 0.7×1.0 cm column of Phenyl-Sepharose CL-4B previously equilibrated with 2 M NaCl. The column was washed stepwise with 2 M NaCl followed by 1 M NaCl and then water. Protein was eluted with a step-wise gradient of 10 to 90 percent ethylene glycol in water, followed by 2% SDS in water. The active fractions were pooled and stored at 4° C. A portion of the pooled enzymatic activity was treated with 1 mM dithiothrietol and dialyzed against 0.2% SDS in water. Alternately, the material was reduced and alkylated with 0.2 M 2-mercaptoethanol in the presence of 8 M urea by solubilizing it in a solution containing EDTA, 0.2 M β-mercaptoethanol and 5-carboxymethyl cysteine. The reaction mixture was dialyzed against 4 liters of water with 3 changes in 24 hours. The material was lyophilized after dialysis.

Immunoblotting—Adult *A. caninum* soluble protein (50 ug) or third stage larval *A. caninum* soluble protein (7.5 ug) was added to 62.5 mM Tris-HCl buffer, pH 6.8, containing 3% SDS, 10% glycerol, and 10 mM dithiothrietol, heated at 80° C. for 5 minutes, and electrophresed on a 10% polyacrylamide gel as described above. An adjacent well containing the molecular weight standards was cut from the gel and stained separately before transfer. The acrylamide gel was transferred onto nitrocellulose as described previously (14). The transfer was carried out non-electrophoretically at room temperature in a Tris-glycine buffer (12.5 mM Tris base, 0.1 M glycine) for 72 hours. All subsequent steps were performed at room temperature.

After protein transfer, the nitrocellulose was removed and incubated in a solution containing 0.3% ficoll 400, 0.3% polyvinylpyrrolidone, and 0.3% BSA. The solution was removed and replaced with 1% BSA in phosphate buffered saline and incubated for 1 hour. The nitrocellulose was then incubated overnight with 0.8 ml of rabbit immune serum (serum collected from a New Zealand White Rabbit immunized and boosted with purified enzyme) in 4.2 ml of Triton-SDS (0.05% Triton X-100, 0.2% SDS in phosphate buffered saline) and then washed 15 minutes (3 times) with Triton-SDS buffer, alone, followed by a 1 hour incubation in 1% BSA in phosphate buffered saline. The nitrocellulose was incubated overnight in $^{125}$I-protein A diluted to a specific activity of 0.15 uCi/ml in Tris buffered saline, pH 8.0, containing 0.05% Tween 20 and 1% BSA, washed as before, and then incubated for 1 hour in 1% BSA in phosphate buffered saline. The nitrocellulose was washed 15 minutes (3 times) with water and air dried before exposure on Kodak X-Omat film with an intensifying screen at −80° C.

Analysis of the Enzyme

Samples of the purified enzyme were subjected to amino acid analysis, to determine percentages of amino acids in the enzyme, as well as the sequence.

To determine the amount of amino acids present in the enzyme, 20 hour and 72 hour acid hydrolyzates were analyzed with a Durrum amino acid analyzer. Half-cystine was determined as cysteic acid by performic oxidation, followed by amino acid analysis of acid hydrolyzates.

The approximate number of amino acid residues as determined by the method spura, is as follows:

| Amino Acid | Residues/Molecule |
|---|---|
| Aspartic Acid/Asparagine | 38 |
| Threonine | 22[1] |
| Serine | 29[1] |
| Glutamic Acid/Glutamine | 31 |
| Proline | N.D.[3] |
| Glycine | 41 |
| Alanine | 37[2] |
| Valine | 29[2] |
| Half-cystine | 5 |
| Methionine | 4 |
| Isoleucine | 21[2] |
| Leucine | 31 |
| Tyrosine | 15[1] |
| Phenylalanine | 10 |
| Tryptophan | N.D.[3] |
| Lysine | 23 |
| Histidine | 6 |
| Arginine | 8 |
| Total | 350 a.a. 36,811 daltons |

[1]Value extrapolated to zero time of hydrolysis.
[2]Value from analysis after 72 hours of hydrolysis.
[3]Not determined by method described.

The helminthic proteolytic enzyme therefore appears to contain approximately 350 amino acid residues, and its weight of 36,811 daltons is in accord with other experiments described herein.

The amino acid sequence of the enzyme has been deduced to some degree. Automated Edman degradation was performed on an Applied Biosystems Inc. model 470A proteins sequences rising modified PTH amino acid analysis.

The sequence of the enzyme, as determined from the N-terminal, has been found to be:

Arg-His-His-Gln-Pro-Lys-Val-Ala-Leu-Leu-Gly-Ala-His-Gly-Gly-Ile

II. Proteolytic and Elastolytic Activity of Homogenates and ES Products of Blood-sucking Nematodes Fibrogenolysis with ES Hookworms of the genus Ancylostoma secrete an anticoagulant which both inhibits the clotting of human plasma and promotes fibrin clot dissolution. This anticoagulant activity is attributable to a 37,000 dalton proteolytic enzyme. The protease can degrade fibrinogen into five smaller polypeptides which intrinsically have anticoagulating properties, convert plasminogen to a mini-plasminogen-like molecule, and hydrolyze a synthetic peptide substrate with specificity for elastolytic enzymes. It is hypothesized that the parasite utilizes this enzyme to prevent blood clotting while feeding on villous capillaries.

Electrophoretic separation of fibrinogen fragments.

$^{125}$-fibrinogen plates. Multi-well Linbro$^R$ plates (Linbro Scientific, Inc., Hamden, Conn.) coated with $^{125}$I-fibrinogen were prepared by the method of Unkeless, et al (Unkeless, J. C., Tobia, A., Ossowski, L., Quigley, J. P., Rifkin, D. B., and E. Reich. 1972. *J. Exp. Med.* 137:85). Radioactivity in solution was determined with a Packard Auto-Gamma Scintillation Spectrometer, model 3002 (Packard Instrument Co., Downers Grove, Ill).

A solution of bovine fibrinogen (6.7 mg/ml) was incubated at 37° in the presence of ES products (0.2 mg/ml). As controls, an equal amount of fibrinogen was incubated either alone or with plasmin. At indicated times aliquots were removed, added to buffer containing 10% glycerol, 3% SDS, and 0.0625 M Tris-HC buffer, pH 6.8, and boiled for 5 minutes. The samples were subjected to SDS-PAGE.

Anticoagulant activity of ES-generated fibrinogen degradation products. Bovine fibrinogen (6.7 mg/ml) was incubated either alone or with 0.01 volume of ES products (0.20 mg/ml protein) for 12-24 hours at 37°. Prothrombin times were measured with various concentrations of citrated plasma and ES-generated fibrinogen degradation products or fibrinogen alone.

Anticlotting properties of ES products. The specificity of the proteolytic activity which could account for the anticlotting effect was sought. Using multi-well plates coated with $^{125}$iodinated fibrinogen, both homogenates and ES products of *A. caninum* were observed to degrade radiolabelled fibrinogen coated on plates. The amount of fibrinogen degraded was proportional to the amount of homogenate or ES products added, and showed no significant amplification by the addition of plasminogen. Thus the protease was not acting as a plasminogen activator.

The ability of ES products to degrade fibrinogen was also demonstrated using SDS-PAGE under nonreduced conditions. ES products catalyzed the degradation of fibrinogen to five major components of molecular weight 223,000, 204,000, 156,000, 122,000 and 80,000 daltons and a minor component at 61,000 daltons. The molecular weight of fibrinogen alone incubated at 37° remained unchanged throughout the experiment, and the molecular weight of the fibrinogen degradation products was different than those observed with plasmin-catalyzed degradation of fibrinogen.

The fibrinogen degradation products resulting from ES digestion, by themselves increased prothrombin time. When 50 μl of fibrinogen (6.7 mg/ml), which had been previously incubated for 12-24 hours at 37° with 0.01 volume of ES products were added to citrated plasma, the prothrombin time was prolonged 80% as compared to a 30% prolongation with 50 μl of fibrinogen (6.7 mg/ml) incubated alone under similar conditions.

Plasminogenolysis with ES Products

Electrophoretic separation of plasminogen fragments. Plasminogen was purified from human plasma by affinity chromatography (Deutsch, D. G., and E. T. Mertz. 1970. *Science.* 170:1095). The plasminogen (2.3 mg/ml) was incubated at 37° in the presence of ES products (0.05 mg/ml protein). As controls, an equal amount of plasminogen was incubated either alone or with 1.0 mU urokinase. At indicated times aliquots were removed, added to buffer containing 10% glycerol, 5% 2-mercaptoethanol, 3% SDS, and 0.0625 M Tris-HCl buffer, pH 6.8, and boiled for 5 minutes. The samples were subjected to SDS-PAGE.

In addition to direct fibrinogenolysis, ES products also catalyzed the cleavage of plasminogen. After a one hour incubation with plasminogen, two polypeptides of 40,000 and 58,000 daltons were formed. The molecular weight of the smaller fragment is similar to that reported for mini-plasminogen (Moroz, L. A. 1981. Blood 58:97) which is formed when leukocyte elastase cleaves plasminogen. This 40,000 dalton fragment was observed by the casein lysis technique to have proteolytic activity. In addition to the two major bands at 40,000 and 58,000 daltons, two minor bands appeared at 39,000 and 65,000 daltons. This heterogeneity may reflect the finding that human plasminogen contains two major components, plasminogen a and b which have slightly different molecular weights (Dano, K., and E. Reich. 1975. *Proteases and Biological Control*). This cleavage by ES products was in contrast to the incubation of plasminogen with urokinase which resulted in two fragments of 68,000 and 28,000 daltons, corresponding to the heavy and light chain of plasmin, respectively. Plasminogen alone showed no degradation during this incubation.

The purified enzyme is observed to catalyze the hydrolysis of elastin. The enzyme hydrolyzes elastase peptide substrate methoxysuccinyl-L-alanyl-L-alanyl-L-propyl-L-valine-4-aminoethyl coumarin on the carboxyl side of the valine residue. The precise cleavage site remains to be determined, however.

The elastase activity was observed against purified ox ligamentum nuchae $^3$H-elastin. An enzyme sample was incubated with $^3$H-elastin (200 ug, 30–40 cpm) in 0.3 ml of 0.1 M Tris HCl, pH 9.0 at 37° C. for 16 hours. Incubation was followed by centrifugation to remove undigested elastin. The amount of $^3$H-label solubilized was determined by counting 0.1 ml aliquots by liquid scintillation.

Elastolytic properties of Hookworm homogenates and ES Products

Assessment of elastolytic activity. Elastolytic activity of hookworm homogenates and ES products was determined using a synthetic peptide substrate covalently linked to a fluorescent leaving group (Castillo, M. J., Nakajima, K., Zimmerman, M., and J.C. Powers. 1979. *Anal. Biochem.* 99:53). The rate of hydrolysis of meosucc-ala-ala-pro-val-AMC (Vega Biochemicals, Tucson, Ariz.) was measured spectrofluorimetrically in a Perkin-Elmer 204 fluorescence spectrophotometer (Perkin-Elmer, Co., Norwalk, Conn.). Various concentrations of either hookworm homogenates or ES products were added to a cuvette containing the substrate (10–50 M) in buffer containing 0.05M TES, 0.50M NaCl, 0.03–0.10 M CaCl$_2$ at pH 7.0 with 10% v/v DMSO at 22° or 37°. The initial rate of increase in the AMC concentration was monitored at excitation and emission wavelengths of 370 nm and 460 nm, respectively.

Elastolytic properties of ES products.

The catalytic cleavage of plasminogen to a mini-plasminogen-like fragment suggested that ES products might have a proteolytic activity which has elastolytic properties. Both hookworm homogenates and ES products could hydrolyze the synthetic substrate meosucc-ala-ala-pro-val-AMC which has specificity for elastolytic enzymes (Castillo, M. J., Nakajima, K., Zimmerman, M., and J. C. Powers. 1979. *Anal. Biochem.* 99:53).

The specific activity for the hydrolysis of the substrate (20 M) at 37° was 0.02 nmoles of AMC released/min/mg protein and 0.21 nmoles of AMC released/min/mg protein for the homogenates and ES products, respectively. This is comparable with 21 nmoles of AMC released/min/mg protein using commercially purified porcine elastase (Elastin Products Co., Pacific, Mo.). The low activity observed for the purified enzyme reflects the suboptimal synthetic substrate concentrations (Castillo, M. J., Nakajima, K., Zimmerman, M., and J. C. Powers. 1979. Anal. Biochem. 99:53) and the pH conditions (pH 7.0 instead of the optimal pH 8.8) used for the experiment.

The time course of secretion in vitro by *A. caninum* of the elastolytic-like protease was followed using the synthetic substrate. *A. caninum* hookworms secrete the protease in linear fashion during the first 9 hours in vitro. Subsequently, the amount of protease released decreases, probably reflecting a decrease in the viability of the worms. This increase in elastolytic activity with time in vitro was paralleled by increasing intensity of the zone of lysis at 37,000 daltons on SDS-PAGE with casein agar.

III. Immunological Aspects of HP Enzyme

From a medical and veterinary standpoint, the proteolytic anticoagulant of the hookworm represents a unique feature available to natural and induced immunological intervention. In support of this is the fact that dogs with repeated infections became immune to *A. caninum* infection, and sera from these dogs neutralized proteolytic enzyme activity in esophogeal extracts from the parasite (Thorson, R. E. 1956. *J. Parasitol* 42:21). During feeding ES products are introduced into the host and eventually elicit protective antibodies. When these protective antibodies inhibit the HP enzymes the antihemostatic mechanism is blocked which allows clot formation, and starvation of the parasite.

In support of this finding is the demonstration on Western blots of the antibodies to the enzymes of 37,000 daltons.

Antibody inhibition of HP enzyme. IgG was obtained from immune dogs by passing serum from these animals over a DEAE-Affigel Blue Column (BIORAD). The effluent was concentrated in an Amicon filter (0.74 mg protein/ml). This material could inhibit protease activity in *A. caninum* ES products by up to 85%. Moreover, 60% of this inhibition could be removed by absorbing the material (DEAE-Affigel effluent) with protein A Sepharose (Pharmacia). This shows that 60% of the inhibitory activity resulted from dog immunoglobulin, with the remainder due to non-specific plasma protease inhibitors (e.g., antitrypsin or 2-antiplasmin and other plasma protease inhibitors).

IV. Preparation of Monoclonal Antibodies to HP Enzyme

Purified *Ancylostoma caninum* HP enzyme is used to immunize BALB/c mice. Following booster immunizations with doses of HP enzymes, the mice are sacrificed and spleen cells harvested. These are then fused with cells of the mouse myeloma line SP1, using the Kohler and Milstein method. Hybridomas which result are then screened with purified HP enzyme using ELISA methods to determine specificity.

The method described supra resulted in the production of ten hybridomas which produced monoclonal antibodies to the HP enzyme. These cell lines were cloned in order to further characterize the monoclonal antibodies.

Ten monoclonal antibodies are characterized, as follows:

| Monoclonal antibody | heavy chain | Class |
| --- | --- | --- |
| MT5H10BA | u | IgM |
| MT5HC8 | u | IgM |
| MT5HA13 | u | IgM |
| 81 3 B 21 | u | IgM |
| 81 2 A14 | u | IgM |
| 81 17 D2 | u | IgM |
| 81 17 B18 | u | IgM |
| 81 17 E4 | u | IgM |
| 81SC3 | u | IgM |
| 81SC4 | u | IgM |

Hybridomas producing the antibodies 81C3 and 81C4 have been deposited at the American Type Culture Collection, accession numbers HB8706, and HB8707, respectively.

V. Vaccination Studies

Experiments were performed on a canine subject to determine in vivo effect of immunization with antibodies to HP enzyme.

Antibodies isolated from sera as described infra were introduced to the canine specimen. Following immunization, the canine specimen is challenged by introduction of *Ancylostoma caninum* worms. Various tests are then conducted, to determine if immunity has become acquired. This is determined by comparing the results obtained from the immunized subject, to subjects which were not immunized. The results follow.

| | Vaccination Experiment | |
| --- | --- | --- |
| Test | Vaccination with Antibody | No Vaccination |
| % drop in Hematocrit | −8.1 | −25.8 ± 5.1 |
| % drop in RBC | −11.9 | −28.0 ± 7.8 |
| % drop in hemoglobin | −8.1 | −27.5 ± 4.5 |
| HCT drop/worm | 0.038 | 0.111 ± .026 |
| ghemoglobin/dl/worm | 0.013 | 0.040 ± .012 |
| RBC/worm | 8,505 | 17,965 ± 4,858 |
| Fecundity *Eggs/gm feces/♀ | 25.2 | 43.8 ± 10.2 |
| Sex Ratio Adult Worms (F/M) | 0.98 | 1.12 |
| Adult Worms | 87 | 105 ± 39 |
| o worm mass | 2.09 mg | 2.68 ± 0.28 |
| ♀worm mass | 2.79 mg | 3.19 ± 0.58 |

The results show that, for each test, the canine specimen immunized with HP enzyme had acquired a degree of immunity to *Ancylostoma caninum* hookworm.

VI. cDNA cloning of Ancylostoma caninum helminthic protease gene

Adult *A. caninum* were isolated from the intestines of infected dogs, washed and stored at −80° C. Total RNA was isolated, and cDNA libraries were constructed from the total RNA. The construction of the library involves synthesizing first strand cDNA using reverse transcriptase, followed by second strand synthesis using Klenow fragments of polymerase I, and reverse transcriptase.

The cDNA is then introduced into the vector gt11. To accomplish this, EcoRI susceptible cleavage sites were blocked by methylation with S-adenosyl-methionine and EcoR1 methylase. Methylated cDNA was ligated to phosphorylated EcoR1 linkers with T4DNA ligase and digested with EcoR1 restriction enzyme.

This procedure resulted in 105 ng of cDNA from total hookworm RNA, and 41 ng when poly(a)+RNA is used. Both preparations were ligated separately into λgt11, which was digested previously with EcoR1 in a ratio of 20–40 ng cDNA/1 g λgt11 DNA. Percentage of recombinants was determined after induction with IPTG in the presence of 5-bromo-4-chloro-3-indolyl-D-galactoside. When total hookworm RNA was used, 20% recombinants were found. When polyA+RNA was used, the library showed 6% recombinants.

The cDNA libraries were both amplified in *E. coli* strain Y 1088. In order to screen, propagation of the λgt11 library was carried out in *E. coli* strain Y 1090.

Screening was done using either polyclonal antiserum to purified 37,000 dalton protease prepared in rabbits, with $^{125}$I-protein A, or $^{32}$P-labelled oligonucleotide, synthesized according to the N-terminal amino acid sequence described supra (i.e., Arg-His-His-Pro-Lys-Val-Ala-Leu-Leu-Gly-Ala-His-Gly-Gly-Ile. The probe which was synthesized was:
CA(T,C),CA(T,C)CA(A,G)CC(T,C,A)AA This 14 base pair probe can be expressed as 32 sequences. It may be used to screen recombinant plaques, and may be used, as well, to identify the presence of the Ancylostoma hookworm in a tissue sample.

What is claimed:

1. Purified helminthic proteolytic enzymes having molecular weight of about 37,000 daltons as determined by electrophoretic separation and isolated from *Ancylostoma caninum* hookworm and having optimum activity at a basic pH.

2. Enzymes of claim 1, having the N-terminal amino acid sequence Arg-His-His-Gln-Pro-Lys-Val-Ala-Leu-Leu-GLy-Ala-His-Gly-Gly-Ile.

3. Enzymes of claim 1, wherein said enzyme comprises approximately 350 amino acid residues.

4. Enzyme of claim 1, wherein said enzyme comprises the following amino acid residues:

| | |
|---|---|
| Aspartic Acid | 38 |
| Threonine | 22 |
| Serine | 29 |
| Glutamic Acid | 31 |
| Glycine | 40 |
| Alanine | 37 |
| Valine | 29 |
| Half-cystine | 5 |
| Methionine | 4 |
| Isoleucine | 21 |
| Leucine | 31 |
| Tyrosine | 15 |
| Phenylalanine | 10 |
| Lysine | 23 |
| Histidine | 6 |
| Arginine | 8 |

5. Purified helminthic proteolytic enzymes having molecular weight of about 37,000 daltons as determined by electrophoretic separation and isolated from *Ancylostoma caninum* hookworm and having optimum activity at a basic pH isolated from *Ancylostoma caninum* hookworm by the method comprising mechanically mincing a quantity of said hookworms to make a homogenate and thereafter separating said enzymes from said homogenate by means of gel electrophoresis or column chromatography.

* * * * *